US006586470B1

(12) United States Patent
Lojek et al.

(10) Patent No.: US 6,586,470 B1
(45) Date of Patent: Jul. 1, 2003

(54) INSECTICIDAL COMPOSITION

(75) Inventors: John S. Lojek, Elmira (CA); Margaret Anne Lojek, Elmira (CA)

(73) Assignee: Ecoval INC, Elmira (CA)

( * ) Notice: Subject to any disclaimer, the term of this patent is extended or adjusted under 35 U.S.C. 154(b) by 0 days.

(21) Appl. No.: 09/787,042

(22) PCT Filed: Aug. 17, 1999

(86) PCT No.: PCT/CA99/00755

§ 371 (c)(1),
(2), (4) Date: May 14, 2001

(87) PCT Pub. No.: WO00/15035

PCT Pub. Date: Mar. 23, 2000

Related U.S. Application Data

(60) Provisional application No. 60/100,316, filed on Sep. 15, 1998.

(51) Int. Cl.[7] .................. A61K 31/19; A61K 31/34; A01N 43/08
(52) U.S. Cl. .................. 514/557; 514/474; 514/574
(58) Field of Search .................. 514/474, 557, 514/574

(56) References Cited

U.S. PATENT DOCUMENTS

| 5,178,795 A | 1/1993 | Roberts | 252/356 |
| 5,393,791 A | 2/1995 | Roberts | 514/762 |
| 5,573,997 A | 11/1996 | Lojek | 504/142 |
| 5,580,567 A | 12/1996 | Roberts | 424/405 |
| 5,690,950 A | 11/1997 | Beadle et al. | 424/405 |
| 5,705,455 A | 1/1998 | Lojek | 504/142 |

FOREIGN PATENT DOCUMENTS

| DE | 4233806 A1 | | 4/1994 |
| HU | 211188 | * | 12/1995 |
| JP | 60069006 | * | 4/1985 |
| JP | 63297303 | | 5/1988 |
| JP | 9132510 | * | 6/1994 |
| JP | 9132510 | | 5/1997 |
| WO | WO93/02555 | | 2/1993 |
| WO | 9302555 | * | 2/1993 |
| WO | WO95/31100 | | 11/1995 |
| WO | 9531100 | * | 11/1995 |
| WO | WO98/18322 | | 5/1998 |

OTHER PUBLICATIONS

Japanese Abstract: XP–002121782, Takihiro et al., "Production of Vinegar–Based Liquid, Harmless to Humans and Livestock, for Controlling Insects in Fruits and Vegetables", 1997.
Japanese Abstract: XP–002121783, Prasanta et al., "Insecticidal Properties of Abcorbic Acid and Acetic Acid on Bihar Hairy Caterpillar Diacrisia Obliqua", 1987.
Japanese Abstarct: XP–002121784, Masaaki et al., "Organic Acids for the Control of Thrips in vegetables", 1989.

* cited by examiner

Primary Examiner—Alton N. Pryor
(74) Attorney, Agent, or Firm—Ohlandt, Greeley, Ruggiero & Perle, L.L.P.

(57) ABSTRACT

An aqueous insecticide composition consisting essentially of acetic acid and at least one additional acid selected from the group consisting of citric acid, malic acid and ascorbic acid.

29 Claims, No Drawings

INSECTICIDAL COMPOSITION

This Application is a 371 of PCT/CA99/00755 filed Aug. 17, 1999 which claims the benefit of Ser. No. 60/100,316 filed Sep. 15, 1998.

FIELD OF THE INVENTION

The present invention relates to aqueous compositions of acetic acid, and especially to aqueous compositions of acetic acid and at least one of citric acid, malic acid and ascorbic acid, that may be used as insecticides. The compositions may additionally contain minor amounts of surfactant, soap and/or propylene glycol.

BACKGROUND OF THE INVENTION

Synergistic combinations of acetic and citric acids are known for use as a herbicide, as disclosed in U.S. Pat. Nos. 5,573,997 and 5,705,455. Such compositions consist essentially of acetic acid and citric acid in weight ratios in the range of about 10:1 to about 0.5:1, and with concentrations of acetic acid that are up to about 10 wt. %.

The herbicidal compositions can be formulated to effectively and rapidly kill all vegetative growth, including normally hard-to-kill weeds as well as grasses. Alternatively, the herbicidal compositions may be formulated as a selective herbicide, for example, to kill common lawn weeds, leaving the grass unaffected. The herbicidal compositions may also be used as defoliants.

In contrast, insecticidal compositions are required to paralyze or kill, depending on the particular method of use, insects that infest a plant, without killing the plant. Thus, insecticides are required to have a complete absence of herbicidal activity, or at most only slight herbicidal activity, so that the host plant of the insects is not killed. If any wilting of the plant is observed by the user of the insecticide, then the insecticide will normally be deemed to be unacceptable. Furthermore, it may be important that the insecticide also exhibit properties such that it may be applied to edible material e.g. vegetables, or be capable of being safely applied to vegetation without risk of harm to animals, including humans. Some such insecticidal compositions are known.

SUMMARY OF THE INVENTION

An insecticidal composition has now been found that is effective against a variety of insects, with no or minimal herbicidal properties. The insecticidal compositions may be formulated to paralyze insects or to kill them, and moreover may be formulated for effectiveness against several kinds of common insects. In addition, the insecticidal compositions are capable of being applied to edible material and other vegetation without risk of harm to animals, including humans. Furthermore, the insecticidal compositions are friendly to the environment.

An aqueous insecticide composition comprising acetic acid and at least one additional acid selected from the group consisting of citric acid, malic acid and ascorbic acid, the ratio of acetic acid to said at least one acid being in the range of 10:1 to 1:1 on a weight basis, the concentration of acetic acid being less than 8 g/l.

In a preferred embodiment of the invention, the concentration of acetic and citric acids is such that the composition does not exhibit herbicidal properties on tomatoes.

An additional aspect of the invention provides use of aqueous compositions of acetic and at least on of citric acid, malic acid and ascorbic acid, the ratio of acetic acid to said at least one acid being in the range of 10:1 to 1:1 on a weight basis, the concentration of acetic acid being less than 8 g/l as an insecticide, especially such use in the absence of herbicidal activity.

A further aspect relates to a method of treatment of insects with an insecticide comprising, spraying the insects with an aqueous insecticide composition comprising acetic acid and at least one of citric acid, malic acid and ascorbic acid, the ratio of acetic acid to said at least one acid being in the range of 10:1 to 1:1 on a weight basis, the concentration of acetic acid being less than 8 g/l.

Further aspects of the invention are as follows:

An aqueous insecticide composition comprising acetic acid in a concentration up to 50 g/l and surfactant.

An aqueous insecticide composition comprising citric acid in concentration up to 25 g/l and surfactant.

An aqueous insecticide composition comprising an insecticidal effective amount of a surfactant, especially Sponto™ 300T surfactant.

DETAILED DESCRIPTION OF THE INVENTION

The present invention relates to aqueous insecticidal compositions of acetic acid, especially aqueous insecticidal compositions of acetic acid and at least one of citric acid, malic and ascorbic acid. However, the invention will be particularly described herein with reference to a preferred embodiment viz. aqueous insecticidal compositions of acetic acid and citric acid.

The combination of acetic and citric acids exhibits synergistic effects as an insecticide, with the resulting composition being more effective as an insecticide than a corresponding composition of acetic acid or citric acid alone at the same concentration. In addition, the insecticidal composition may be formulated such that the concentration of acetic and citric acids is such that the composition does not exhibit herbicidal properties, especially herbicidal properties with respect to tomatoes, cabbage, roses and peppers, broad leaf plants and/or other vegetation.

In embodiments, the composition of the invention comprises a synergistic combination of acetic acid and citric acid, in aqueous solution. The acetic acid component is conveniently provided by domestic white vinegar while the citric acid is conveniently provided by lemon juice or juices of other citrus fruits. It is understood, however, that industrial sources of either or both of these components may be used. For instance, the composition may be formulated using glacial acetic acid.

The weight ratio of acetic acid to citric acid in the insecticidal composition may vary over a wide range, for instance, in the range of from about 10:1 to about 1:1, preferably in the range of 4:1 to 1:1, on a weight basis.

In embodiments, the weight ratio of acetic acid to citric acid is in the range of 4:1 to about 2:1.

The insecticidal composition in use may contain up to 100 g/l of acetic acid and 50 g/l of citric acid, with the preferred amount of acetic acid being up to 10 g/l and especially up to 4 g/l.

The composition should contain at least 1 g/l of acetic acid and 0.5 g/l of citric acid. Preferred compositions contain about 4 g/l of acetic acid and 2 g/l of citric acid.

The insecticidal activity of the combination of acetic acid and citric acid may be enhanced by addition of surfactants, vegetable oils, alkylene glycol and/or soap. Although soap is known for use in insecticidal compositions, the amount of soap added to the compositions of the present invention is less than that normally used for insecticidal compositions in which soap is the active ingredient.

It is believed that a wide variety of surfactants may be used.

Examples of alkylene glycols include propylene glycol.

Examples of soaps include insecticidal soaps.

A particularly preferred composition contains acetic acid, citric acid and surfactant, especially a surfactant available as Sponto™ 300T. Other surfactants may be used. The amount of surfactant should be in the range of 0.1–40 g/l, preferably 1–5 g/l.

In another embodiment of the invention, the citric acid may be replaced in whole or in part with malic acid and/or ascorbic acid. Thus, the composition may be acetic acid with one or more acids selected from the group consisting of citric acid, malic acid and ascorbic acid. Concentration and ratios of the acetic acid and other acid have been discussed above with respect to use of citric acid.

In further embodiments, acetic acid may be used with surfactant as an insecticide, with or without added citric or other acid.

In still further embodiments, citric acid may be used with surfactant as an insecticide, with or without added acetic or other acid.

The insecticidal composition may be formulated so as to be effective on one or more of a variety of insects. In addition, the insecticidal composition may be formulated so as to kill the insects or to merely paralyze the insects. In the latter instance, it might be beneficial to be able to spray vegetation e.g. a house plant, so as to paralyze the insects which are then removed from the location of the house plant. Such use could be beneficial if higher concentrations of the insecticide might be harmful to the plant.

It is believed that surfactants, soaps and propylene glycol aid in effecting penetration of the composition of acetic and citric acids into the insect, to increase its effectiveness. Thus, surfactants, soaps and propylene glycol tend to increase the toxicity of the acids. However, the increase in toxicity may be dependent on the insect, and the examples herein show instances of adverse or antagonistic effects. For example, addition of surfactant and soap had antagonistic effects in the effectiveness of acetic acid and citric acid on flea beetles but not on corn root worm.

In the examples below, unless indicated to the contrary, individual insects were counted and placed in a clean glass beaker, where they were sprayed with the insecticidal composition being tested. The insects were then immediately transferred to a clean, dry glass flask and covered with paper tissue. The insects remained in the latter flasks for a period of 24 hours, at which time the insects were inspected.

The insecticidal compositions being tested were formulated in aqueous solution. The amounts of the ingredients are specified in the examples, and unless stated otherwise, are expressed in grams/litre.

The present invention is illustrated by the following examples.

EXAMPLE I

A variety of compositions were prepared, as indicated in Table 1 below.

The compositions were tested on Northern corn root worm adults (diabrotica longiscornis). The insects were treated and tested as indicated above.

The results obtained are given in Table 1.

Wilson's Insecticidal Soap™ is alkanolamine salts of fatty acids, registered under No. 21111 of the P.C.P. Act. Wilson's Insecticidal Soap is a 25% concentrate in water, and a typical usage is 50 ml of concentrate in one litre of water. Complete coverage of top and bottom of a leaf is recommended, or immersion of the plant in solution.

It was found a solution of acids as used herein and soap (50 g/L soap, with 4 acetic acid and 2 g citric acid (litre)) resulted in formation of a precipitate (curds) in a short period of time e.g. 15 minutes, indicating that combinations of acid and soap were not compatible for use as an insecticide.

TABLE 1

| Sample | Solution* | Dead | Alive | % Control |
|---|---|---|---|---|
| 1 | 4 g aa | 0 | 10 | 0 |
| 2 | 2 g ca | 0 | 10 | 0 |
| 3 | 4 g aa + 2 g ca | 1 | 9 | 10 |
| 4 | 1 g Surf | 0 | 10 | 0 |
| 5 | 5 g Surf | 6 | 4 | 60 |
| 6 | 4 g aa + 2 g ca + 1 g Surf | 1 | 9 | 10 |
| 7 | 4 g aa + 2 g ca + 1 g Surf + 50 g PG | 4 | 6 | 40 |
| 8 | 5 g Soap | 0 | 10 | 0 |
| 9 | 10 g Soap | 0 | 10 | 0 |
| 10 | 50 g Soap | 4 | 6 | 40 |
| 11 | 4 g aa + 2 g ca + 10 g Soap | 6 | 4 | 60 |
| 12 | 2 g aa + 1 g ca + 5 g Surf | 8 | 2 | 80 |
| 13 | 50 g aa + 25 g ca | 10 | 0 | 100 |
| 14 | 12 g aa + 6 g ca | 1 | 9 | 10 |
| 15 | 12 g aa | 0 | 10 | 0 |
| 16 | 12 g aa + 6 g ca + 1 g Surf | 10 | 0 | 100 |
| 17 | 50 g aa + 0.1 g Surf | 10 | 0 | 100 |
| 18 | 50 g aa | 3 | 7 | 30 |
| 19 | 25 g ca | 2 | 8 | 20 |
| 20 | 25 g ca + 0.1 g Surf | 3 | 7 | 30 |

Notes:
aa = acetic acid
ca = citric acid
PG = Propylene Glycol
Surf = Surfactant (Sponto ™ 300T)
Soap = Wilson's Insecticidal Soap ™ concentrate The results show that acetic acid at 50 g/l gives partial control, as does citric acid at 25 g/l. However, the combination of acetic acid at 50 g/l and citric acid at 25 g/l gives 100% control.

Addition of the surfactant allows a major reduction in concentration of acids, while still providing 100% control; for example Sample 14 with 12 g/l of acetic acid and 6 g/l of citric acid gave 10% control, but addition of 1 g/l of surfactant increased the control to 100% (Sample 16). The surfactant at 1 g/l caused no mortality (Sample 4).

It is known that soaps are insecticidal, and the soap tested is an insecticidal soap. The results show that the soap at 50 g/l, based on the concentrate, gave only 40% control. At a concentration of 10 g/l of concentrate, there was no control. Combinations with acetic and citric acid gave substantially higher levels of control.

Combinations of acetic acid and citric acid with propylene glycol, surfactant and/or soap exhibited varying degrees of effectiveness against Northern corn root worm adults.

The results show that acetic acid plus citric acid are synergistic in activity and that this synergistic activity is enhanced by addition of the surfactant, but less so by addition of much higher levels of insecticidal soap.

This example shows that insecticides based on combinations of acetic and citric acids are effective insecticides.

EXAMPLE II

The procedure was repeated with flea beetles. The results obtained were as follows:

TABLE 2

| Sample | Solution* | Dead | Alive | % Control |
|---|---|---|---|---|
| 22 | 4 g aa + 2 g ca + 5 g Surf | 10 | 0 | 100 |
| 23 | 4 g aa + 2 g ca + 1 g Surf | 10 | 0 | 100 |
| 24 | 4 g aa + 2 g ca + 0.1 g Surf | 10 | 0 | 100 |
| 25 | 1 g Surf | 0 | 10 | 0 |
| 26 | 10 g Soap | 0 | 10 | 0 |
| 27 | 4 g aa + 2 g ca + 10 g Soap | 6 | 4 | 60 |
| 28 | 50 g Soap | 10 | 0 | 100 |
| 29 | 4 g aa + 2 g ca | 0 | 10 | 0 |

Notes:
aa = acetic acid
ca = citric acid
PG = Propylene Glycol
Surf = Surfactant (Sponto ™ 300T)
Soap = Wilson's Insecticidal Soap ™ concentrate This example shows that compositions of acetic acid, citric acid and surfactant were effective insecticidal compositions for flea beetles, but addition of soap to such compositions reduced the effectiveness. Thus, in some instances, the compositions of the invention need to be formulated to be effective against particular insects.

EXAMPLE III

The procedure was repeated with rose aphids. The results obtained given in Table 3.

TABLE 3

| Sample | Solution* | Dead | Alive | % Control |
|---|---|---|---|---|
| 30 | 4 g aa + 2 g ca | 0 | 10 | 0 |
| 31 | 12 g aa + 6 g ca | 10 | 0 | 100 |
| 32 | 2 g aa + 1 g ca + 1 g Surf | 10 | 0 | 100 |
| 33 | 4 g aa + 2 g ca + 0.1 g Surf | 8 | 2 | 80 |
| 34 | 10 g Soap | 10 | 0 | 100 |

Notes:
aa = acetic acid
ca = citric acid
PG = Propylene Glycol
Surf = Surfactant (Sponto ™ 300T)
Soap = Wilson's Insecticidal Soap ™ concentrate This example shows the effect of concentration on effectiveness against rose aphids. Alternatively, addition of surfactant or soap substantially increased effectiveness.

EXAMPLE IV

A solution of 4 g of acetic acid, 2 g citric acid, 1 g surfactant and 50 g of propylene glycol was tested with mites and with both potato beetle adults and larvae. In all instances, 100% of the insects were killed.

EXAMPLE V

The procedure of Example I was repeated with rose loopers. The results obtained are given in Table 4.

TABLE 4

| Sample | Solution* | Dead | Alive | % Control |
|---|---|---|---|---|
| 35 | 10 g aa Soap | 10 | 0 | 100 |
| 36 | 4 g aa + 2 g ca | 0 | 10 | 0 |
| 37 | 12 g aa + 6 g ca | 10 | 0 | 100 |

TABLE 4-continued

| Sample | Solution* | Dead | Alive | % Control |
|---|---|---|---|---|
| 38 | 2 g aa + 1 g ca + 1 g Surf | 10 | 0 | 100 |
| 39 | 4 g aa + 2 g ca + 0.1 g Surf | 8 | 2 | 80 |

Notes:
aa = acetic acid
ca = citric acid
PG = Propylene Glycol
Surf = Surfactant (Sponto ™ 300T)
Soap = Wilson's Insecticidal Soap ™ concentrate

EXAMPLE VI

Compositions of (i) 4 g/l acetic acid, 2 g/l citric acid and 1 g/l of Sponto™ 300T and (ii) 4 g/l acetic acid, 2 g/l citric and 5 g/l of Sponto™ 300T surfactant were tested on cabbage, roses, peppers and tomatoes.

No herbicidal effects were noticed.

In addition to the above examples, it has been found that with a number of insects e.g. aphids, fleas, cabbage worms, mites, thrips and beetles, compositions of the invention cause rapid or even instantaneous paralysis. The insects may recover in time, e.g. a period of 30 minutes to two hours. However, if the composition is fatal, rather than causing paralysis, the insects become paralyzed and exhibit a change of colour and/or shape. Some insects e.g. worms, aphids and thrips, tend to go flat. An area of fluid is often noted around the insect, which is believed to be an indication of dehydration effects.

The present invention provides aqueous insecticidal compositions that are environmentally acceptable. The compositions are synergetic insecticidal compositions of acetic and citric acid, optionally containing surfactant, soap and/or propylene glycol. A preferred composition contains acetic acid and citric acid and surfactant.

EXAMPLE VII

The procedure of Example III was repeated, except that citric acid was replaced with malic acid.

The result obtained was as follows:

TABLE 5

| Sample | Solution* | Dead | Alive | % Control |
|---|---|---|---|---|
| 40 | 6 g aa + 3 g ma + 1 g Surf | 8 | 2 | 80 |

Notes:
aa = acetic acid
ma = malic acid
Surf = Surfactant (Sponto ™ 300T)

This example shows that combinations of acetic acid and malic acid have effectiveness as an insecticide.

What is claimed is:

1. An aqueous insecticide composition consisting essentially of acetic acid and at least one additional acid selected from the group consisting of citric acid, malic acid and ascorbic acid, the ratio of acetic acid to said at least one acid being in the range of 10:1 to 1:1 on a weight basis, the concentration of acetic acid being less than 8 g/L, thereby exhibiting substantially no herbicidal properties.

2. The aqueous insecticide composition of claim 1 in which said at least one acid is citric acid.

3. The aqueous insecticide composition of claim 1 in which said at least one acid is malic acid.

4. The aqueous insecticide composition of claim 1 in which said at least one acid is ascorbic acid.

5. The aqueous insecticide composition of any one of claims 1–4 in which the ratio is in the range of 4:1 to 1:1 on a weight basis.

6. The aqueous insecticide composition of claim 5 in which the ratio is in the range of 4:1 to 2:1 on a weight basis.

7. The aqueous insecticide composition of any one of claims 1–6 in which the concentration of acetic acid is up to 4 g/l.

8. The aqueous insecticide composition of any one of claims 1–7 in which the concentration of acids is such that the composition does not exhibit herbicidal properties on tomatoes.

9. An aqueous insecticide composition consisting essentially of acetic acid; at least one additional acid selected from the group consisting of citric acid, malic acid and ascorbic acid, the ratio of acetic acid to said at least one acid being in the range of 10:1 to 1:1 on a weight basis, the concentration of acetic acid being less than 8 g/L, thereby exhibiting substantially no herbicidal properties; and at least one of a surfactant, a soap or propylene glycol.

10. An aqueous insecticide composition consisting essentially of acetic acid; at least one additional acid selected from the group consisting of citric acid, malic acid and ascorbic acid, the ratio of acetic acid to said at least one acid being in the range of 10:1 to 1:1 on a weight basis, the concentration of acetic acid being less than 8 g/L; and insecticidal soap.

11. An aqueous insecticide composition of claim 9 consisting essentially of acetic acid, citric acid and surfactant.

12. An aqueous insecticide composition consisting essentially of acetic acid, citric acid and soap, the ratio of acetic acid to citric acid being in the range of 10:1 to 1:1 on a weight basis, the concentration of acetic acid being less than 8 g/L.

13. An aqueous insecticide composition of claim 9 consisting essentially of acetic acid, citric acid and propylene glycol.

14. The aqueous insecticide composition of claim 9 in which the composition has a surfactant, said surfactant being in a concentration of 0.1 to 40 g/l.

15. An aqueous insecticide composition of claim 14 in which the surfactant has a concentration of between 1–5 g/l.

16. The aqueous insecticide composition of claim 15 in which the surfactant is a mixture of anionic and nonionic surfactant.

17. The aqueous insecticide composition of claim 14 in which the amount of surfactant is at least 5 g/l.

18. A method of treating flea beetles comprising the step of contacting said flea beetles with an aqueous insecticide composition of claim 11.

19. A method of the treatment of insects with an insecticide, comprising spraying said insects with said aqueous insecticide composition of claim 1.

20. An aqueous insecticide composition consisting essentially of acetic acid and surfactant, wherein the concentration of said acetic acid being up to 50 g/L.

21. The aqueous insecticide composition of claim 20 in which said surfactant being in a concentration of 0.1 to 40 g/l.

22. An aqueous insecticide composition consisting essentially of a surfactant in an amount of the range of 0.1 to 4.0 g/L, wherein the surfactant is a mixture of anionic and non-ionic surfactant.

23. The aqueous insecticide composition of claim 22 in which the concentration of said surfactant is in the range of 1–5 g/l.

24. An aqueous insecticide composition consisting essentially of citric acid and surfactant, wherein the concentration of citric acid being up to 25 g/L.

25. The aqueous insecticide composition of claim 24 in which said surfactant being in a concentration of 0.1 to 40 g/l.

26. An aqueous insecticide composition consisting essentially of an insecticidal effective amount of a surfactant.

27. The aqueous insecticide composition of claim 26 in which the surfactant is a mixture of anionic and nonionic surfactant.

28. The aqueous insecticide composition of claim 27 in which the concentration of the surfactant is in the range of 0.1 to 40 g/l.

29. The aqueous insecticide composition of claim 28 in which the concentration of said surfactant is in the range of 1–5 g/l.

* * * * *